United States Patent
Kim et al.

(10) Patent No.: US 7,200,440 B2
(45) Date of Patent: Apr. 3, 2007

(54) CARDIAC CYCLE SYNCHRONIZED SAMPLING OF IMPEDANCE SIGNAL

(75) Inventors: Jaeho Kim, Redmond, WA (US); Quan Ni, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 499 days.

(21) Appl. No.: 10/612,388

(22) Filed: Jul. 2, 2003

(65) Prior Publication Data

US 2005/0004610 A1 Jan. 6, 2005

(51) Int. Cl.
*A61N 1/365* (2006.01)

(52) U.S. Cl. .......................................... 607/18; 607/17

(58) Field of Classification Search .................. None
See application file for complete search history.

(56) References Cited

U.S. PATENT DOCUMENTS

| | | | |
|---|---|---|---|
| 3,593,718 A | 7/1971 | Krasner | |
| 4,291,699 A | 9/1981 | Geddes et al. | |
| 4,510,944 A | 4/1985 | Porges | |
| 4,519,395 A | 5/1985 | Hrushesky | |
| 4,596,251 A | 6/1986 | Plicchi et al. | |
| 4,686,987 A | 8/1987 | Salo et al. | |
| 4,702,253 A | 10/1987 | Nappholz et al. | |
| 4,722,351 A | 2/1988 | Phillipps et al. | |
| 4,773,401 A | 9/1988 | Citak et al. | |
| 4,781,201 A | 11/1988 | Wright et al. | |
| 4,827,935 A | 5/1989 | Geddes et al. | |
| 4,830,008 A | 5/1989 | Meer | |
| 4,858,611 A | 8/1989 | Elliott | |
| 4,901,725 A | 2/1990 | Nappholz et al. | |
| 4,930,518 A | 6/1990 | Hrushesky | |
| 4,960,129 A | 10/1990 | dePaola et al. | |
| 4,966,146 A | 10/1990 | Webb et al. | |
| 5,014,698 A | 5/1991 | Cohen | |
| 5,063,927 A | 11/1991 | Webb et al. | |
| 5,074,303 A | 12/1991 | Hauck | |
| 5,137,019 A | 8/1992 | Pederson et al. | |

(Continued)

FOREIGN PATENT DOCUMENTS

DE 2805482 3/1987

(Continued)

OTHER PUBLICATIONS

Hauck, John A., "A Minute Ventilation Sensor Derived from Intrathoracic Electric Impedance as a Cardiac Pacemaker Rate Modulator", *University of Minnesota Master Thesis*, (Jun. 1993), pp. 80-86 & 97.

*Primary Examiner*—Carl Layno
(74) *Attorney, Agent, or Firm*—Schwegman, Lundberg, Woessner, & Kluth

(57) ABSTRACT

A cardiac rhythm management device for obtaining transthoracic impedance. The device comprises a sensor for obtaining a signal indicative of an action of a heart, an impedance measurement circuit adapted to measure transthoracic impedance and a processor for utilizing the signal indicative of the action of the heart to sample the transthoracic impedance at sampling intervals commenced by fiducial markers in the signal indicative of the action of the heart, where the sampling of the impedance signal removes the component of a stroke volume of the heart from the signal and thereby provides lung ventilation information.

45 Claims, 9 Drawing Sheets

U.S. PATENT DOCUMENTS

| | | | |
|---|---|---|---|
| 5,156,147 A | 10/1992 | Warren et al. | |
| 5,179,946 A | 1/1993 | Weiss | |
| 5,197,467 A | 3/1993 | Steinhaus et al. | |
| 5,201,808 A | 4/1993 | Steinhaus et al. | |
| 5,249,572 A | 10/1993 | Bonnet | |
| 5,269,301 A | 12/1993 | Cohen | |
| 5,271,395 A | 12/1993 | Wahlstrand et al. | |
| 5,273,034 A | 12/1993 | Nilsson | |
| 5,284,136 A | 2/1994 | Hauck et al. | |
| 5,300,093 A | 4/1994 | Koestner et al. | |
| 5,303,702 A | 4/1994 | Bonnet et al. | |
| 5,318,597 A | 6/1994 | Hauck et al. | |
| 5,341,811 A | 8/1994 | Cano | |
| 5,379,776 A | 1/1995 | Murphy et al. | |
| 5,391,190 A | 2/1995 | Pederson et al. | |
| 5,423,870 A | 6/1995 | Olive et al. | |
| 5,441,524 A | 8/1995 | Rueter et al. | |
| 5,469,859 A | 11/1995 | Tsoglin et al. | |
| 5,507,785 A | 4/1996 | Deno | |
| 5,522,860 A | 6/1996 | Molin et al. | |
| 5,524,632 A | 6/1996 | Stein et al. | |
| 5,531,772 A | 7/1996 | Prutchi | |
| 5,540,733 A | 7/1996 | Testerman et al. | |
| 5,562,711 A * | 10/1996 | Yerich et al. | 607/17 |
| 5,562,712 A | 10/1996 | Steinhaus et al. | |
| 5,626,622 A | 5/1997 | Cooper | |
| 5,626,624 A | 5/1997 | Schaldach et al. | |
| 5,685,316 A | 11/1997 | Schookin et al. | |
| 5,718,720 A | 2/1998 | Prutchi et al. | |
| 5,722,997 A | 3/1998 | Nedungadi et al. | |
| 5,755,742 A | 5/1998 | Schuelke et al. | |
| 5,792,194 A | 8/1998 | Morra | |
| 5,792,208 A | 8/1998 | Gray | |
| 5,800,470 A | 9/1998 | Stein et al. | |
| 5,817,135 A | 10/1998 | Cooper et al. | |
| 5,817,136 A | 10/1998 | Nappholz et al. | |
| 5,824,020 A | 10/1998 | Cooper | |
| 5,824,029 A | 10/1998 | Weijand et al. | |
| 5,836,976 A | 11/1998 | Min et al. | |
| 5,921,940 A | 7/1999 | Verrier et al. | |
| 5,935,081 A | 8/1999 | Kadhiresan | |
| 5,987,356 A | 11/1999 | DeGroot | |
| 6,015,388 A | 1/2000 | Sackner et al. | |
| 6,021,351 A | 2/2000 | Kadhiresan et al. | |
| 6,022,322 A | 2/2000 | Prutchi | |
| 6,026,320 A | 2/2000 | Carlson et al. | |
| 6,044,294 A | 3/2000 | Mortazavi et al. | |
| 6,073,048 A | 6/2000 | Kieval et al. | |
| 6,076,015 A * | 6/2000 | Hartley et al. | 607/20 |
| 6,135,970 A | 10/2000 | Kadhiresan et al. | |
| 6,161,042 A | 12/2000 | Hartley et al. | |
| 6,358,201 B1 | 3/2002 | Childre et al. | |
| 6,370,424 B1 | 4/2002 | Prutchi | |
| 6,415,183 B1 | 7/2002 | Scheiner et al. | |
| 6,449,509 B1 | 9/2002 | Park | |
| 6,459,929 B1 | 10/2002 | Hopper et al. | |
| 6,463,326 B1 | 10/2002 | Hartley et al. | |
| 6,480,733 B1 | 11/2002 | Turcott | |
| 6,522,914 B1 | 2/2003 | Huvelle | |
| 6,529,772 B2 | 3/2003 | Carlson et al. | |
| 6,561,986 B2 * | 5/2003 | Baura et al. | 600/526 |
| 6,647,289 B2 | 11/2003 | Prutchi | |
| 6,868,346 B2 * | 3/2005 | Larson et al. | 702/45 |
| 7,062,326 B2 | 6/2006 | Huvelle et al. | |
| 7,101,339 B2 | 9/2006 | Daum et al. | |
| 2003/0032991 A1 * | 2/2003 | Poore | 607/32 |
| 2003/0105499 A1 | 6/2003 | Hartley et al. | |
| 2003/0114891 A1 | 6/2003 | Hiebert et al. | |
| 2004/0049237 A1 | 3/2004 | Larson et al. | |
| 2004/0102908 A1 | 5/2004 | Larson et al. | |
| 2005/0004609 A1 | 1/2005 | Stahmann et al. | |
| 2005/0065443 A1 | 3/2005 | Ternes | |
| 2005/0096704 A1 | 5/2005 | Freeberg | |

FOREIGN PATENT DOCUMENTS

| | | |
|---|---|---|
| EP | 0003567 | 8/1979 |
| EP | 0447024 A2 | 9/1991 |
| EP | 0555988 | 8/1993 |
| EP | 0709058 A1 | 1/1996 |
| EP | 0702977 A2 | 3/1996 |
| EP | 0765632 A2 | 4/1997 |
| FR | 2305168 | 10/1976 |
| WO | WO-94/06512 A1 | 3/1994 |
| WO | WO-98/14240 | 4/1998 |

* cited by examiner

CARDIAC CYCLE SYNCHRONIZED SAMPLING OF IMPEDANCE SIGNAL

TECHNICAL FIELD

This document relates generally to implantable devices, and, in particular, to a system and method for obtaining transthoracic impedance information.

BACKGROUND

Many systems implantable into a patient's thorax include a pulse generator and an arrangement of endocardial or intravascular leads (hereinafter referred to as "leads"). The pulse generator delivers electrical stimuli to tissue via the leads to provide a desired therapy. For example, implantable pacemakers deliver timed sequences of low energy electrical stimuli, called pace pulses, to the heart via an intravascular lead. By properly timing the delivery of pace pulses, the heart can be induced to contract in proper rhythm, greatly improving its pumping efficiency. Implantable defibrillators are devices capable of delivering higher energy electrical stimuli to the heart. A defibrillator is capable of delivering a high-energy electrical stimulus via leads that is sometimes referred to as a defibrillation countershock. The countershock interrupts a fibrillation, allowing the heart to reestablish a normal rhythm for efficient pumping of blood. These systems are able to sense cardiac signals and deliver therapy to the heart based on such signals.

The arrangement of the leads of such systems in the thorax region allows for other physiologic signals to be sensed. One type of physiologic signal is the transthoracic (i.e. across the chest) impedance of a patient with such a device. One approach to measure transthoracic impedance is described in Hartley et al., U.S. Pat. No. 6,076,015 "RATE ADAPTIVE CARDIAC RHYTHM MANAGEMENT DEVICE USING TRANSTHORACIC IMPEDANCE," assigned to the assignee of the present application and which is incorporated herein by reference. The transthoracic impedance signal includes multiple components. A first component of the impedance varies with a patient's breathing and is useful in determining how fast (breathing rate) or how deeply (lung tidal volume) a patient is breathing. Information concerning a patient's breathing over a period of time is useful to an implantable pacemaker system as a metabolic indication that the patent's heart rate needs to be adjusted. However, the measurement of this respiratory component of the transthoracic impedance is complicated by other components of the impedance signal. For example, transthoracic impedance also varies with the volume of blood in a patient's heart and thus varies during a patient's heartbeat or cardiac cycle. This component is sometimes referred to as the cardiac stroke volume. This stroke volume component is close in frequency to the respiratory component. The closeness of the frequencies makes it difficult to separate the two components from each other. Previous solutions to the problem have used filtering circuitry to remove all but the breathing component of the transthoracic signal. However, because implantable systems are battery powered and are implanted for long periods of time, methods that perform a function with lower power consumption extending the battery life are valuable in such systems. Thus there is a need for a device and method to measure the respiratory component of the transthoracic impedance that has low power consumption.

SUMMARY

This document discusses a cardiac rhythm management device and method for obtaining impedance information from a thorax region of a patient. The device comprises a sensor for obtaining a signal indicative of an action of a heart, an impedance measurement circuit adapted to measure transthoracic impedance and a processor for utilizing the signal indicative of the action of the heart to sample the transthoracic impedance at sampling intervals commenced by fiducial markers in the signal indicative of the action of the heart, where the sampling of the impedance signal removes the component of a stroke volume of the heart from the signal and thereby providing lung ventilation information.

The method of measuring a transthoracic impedance comprises detecting intrinsic heart activity signals, applying a predetermined pulsed current stimulus across a thorax region of a patient in a predetermined time relationship to a fiducial marker, sampling a voltage across the thorax region when applying the predetermined pulsed current stimulus, and calculating an impedance from the measured voltage and the predetermined pulsed current stimulus.

This summary is intended to provide an overview of the subject matter of the present application. It is not intended to provide an exclusive or exhaustive explanation of the invention. The detailed description is included to provide further information about the subject matter of the preset patent application.

BRIEF DESCRIPTION OF THE DRAWINGS

In the drawings like numerals refer to like components throughout the several views.

DETAILED DESCRIPTION

In the following detailed description, reference is made to the accompanying drawings which form a part hereof, and in which is shown by way of illustration specific embodiments in which the invention may be practiced. It is to be understood that other embodiments may be utilized and structural changes may be made without departing from the scope of the present invention.

As discussed previously, the measurement of the respiratory component of the transthoracic impedance is complicated by the presence of the stroke volume component of the impedance signal. Because the stroke volume component is present due to the filling and emptying of the heart with blood, this component is synchronized to heartbeats. Implantable systems are able to sense intrinsic activity signals associated with heartbeats. The implantable systems are further able to generate fiducial markers in response to occurrences of such an activity signals. As an example, one of these activity signals is a QRS complex. A QRS complex is the activity signal associated with the process of the ventricular chambers depolarizing or contracting to empty the chambers of blood. In general, the volume of blood in the heart at an occurrence of an activity signal is fairly consistent from one occurrence of the signal to the next. Thus, the stroke volume component of the transthoracic impedance will also be fairly consistent at each occurrence of the signal. If the transthoracic impedance is sampled synchronously only when the implantable system generates a specific fiducial marker, the stroke volume component will be constant during the sampling and the respiratory signal is easily extracted from the transthoracic impedance signal. Examples of intrinsic heart activity signals sensed by implantable systems and useful for sampling include an onset of a P-wave, an onset of a QRS complex, an R-wave peak, or a T-wave peak.

Figure 1:
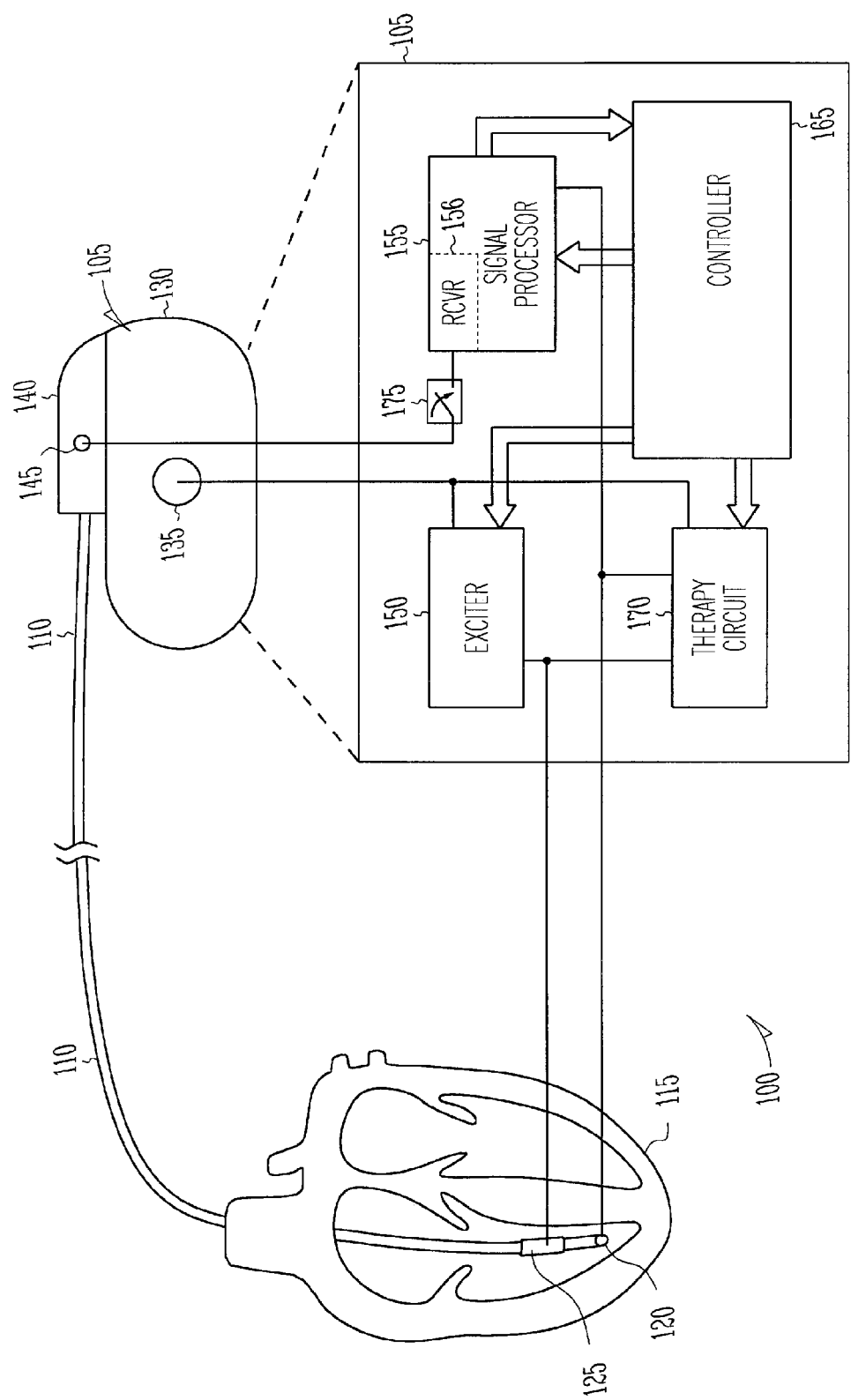
FIG. 1 shows a block diagram of a cardiac rhythm management system that samples transthoracic impedance in a predetermined time relationship to a fiducial marker.

FIG. 1 shows one embodiment of a system 100 for sampling the transthoracic impedance commenced at the occurrence of a fiducial marker. This embodiment of the system includes pulse generator 105 and endocardial lead 110. Lead 110 is shown coupled to pulse generator 105. Lead 110 is a multi-conductor lead and includes tip electrode 120 coupled to a first conductor and ring electrode 125 coupled to a second lead conductor. Pulse generator 105 includes a hermetically sealed outer housing 130. Outer housing 130 (sometimes referred to as the case or can) is comprised of a conducting material such as titanium, and is covered by an insulating material such as silicone rubber. A hole or window in the insulating material allows a third electrode 135 to be formed from the can 130 of pulse generator 105.

Pulse generator 105 also includes a header 140 for receiving the lead 110 and is formed from an insulating material such as molded plastic. Header 140 also includes a fourth electrode 145. Such a four-electrode system is described in Hauck et al., U.S. Pat. No. 5,284,136 "DUAL INDIFFERENT ELECTRODE PACEMAKER," assigned to the assignee of the present application and which is incorporated herein by reference. Other embodiments of the system include a two or three electrode system. In the embodiment shown, lead 110 is implanted in the right ventricle of a heart 115. In this embodiment, the impedance sampling may begin, for example, at a fiducial marker indicating the onset of a QRS complex, at a fiducial marker indicating a peak of the R-wave, or at a fiducial marker indicating a peak of the T-wave.

FIG. 1 also illustrates portions of pulse generator 105. Therapy circuit 170 provides electrical pacing stimuli to the heart 115. Such pacing stimuli include providing bipolar pacing between tip electrode 120 and ring electrode 125 to initiate a contraction of the ventricles. Controller 165 adjusts the rate of the pacing stimuli delivered by the therapy circuit 170. Signal Processor 155 senses an intrinsic heart activity signal. When signal processor 155 senses the onset of an intrinsic heart activity signal, controller 165 initiates an impedance measurement. Exciter 150 delivers an electrical excitation signal, such as a pulsed current stimulus or any other suitable measurement stimulus, to heart 115. In one embodiment, exciter 150 delivers a predetermined current stimulus between ring electrode 125 and can electrode 135. In other embodiments exciter 150 delivers a current stimulus between any other suitable combinations of electrodes. Signal processor 155 senses the response to the excitation signal. In one embodiment, signal processor 155 senses the response between tip electrode 120 and header electrode 145. In other embodiments, signal processor 155 senses the response between any other suitable combinations of electrodes. Receiver 156 of the signal processor 155 receives a voltage through sampling element 175 in response to the onset of an intrinsic heart activity signal and the current stimulus. In the embodiment shown sampling element 175 is placed in series with header electrode 145 and the receiver 156. In another embodiment the sampling element is placed in series with the lead electrodes 120, 125 and the receiver 156. The signal processor 155 then measures the voltage by any method known in the art such as by an Analog to Digital converter. Transthoracic impedance is obtained from the predetermined current stimulus and the measured voltage. The transthoracic impedance may then be used to determine respiratory information.

Figure 2:
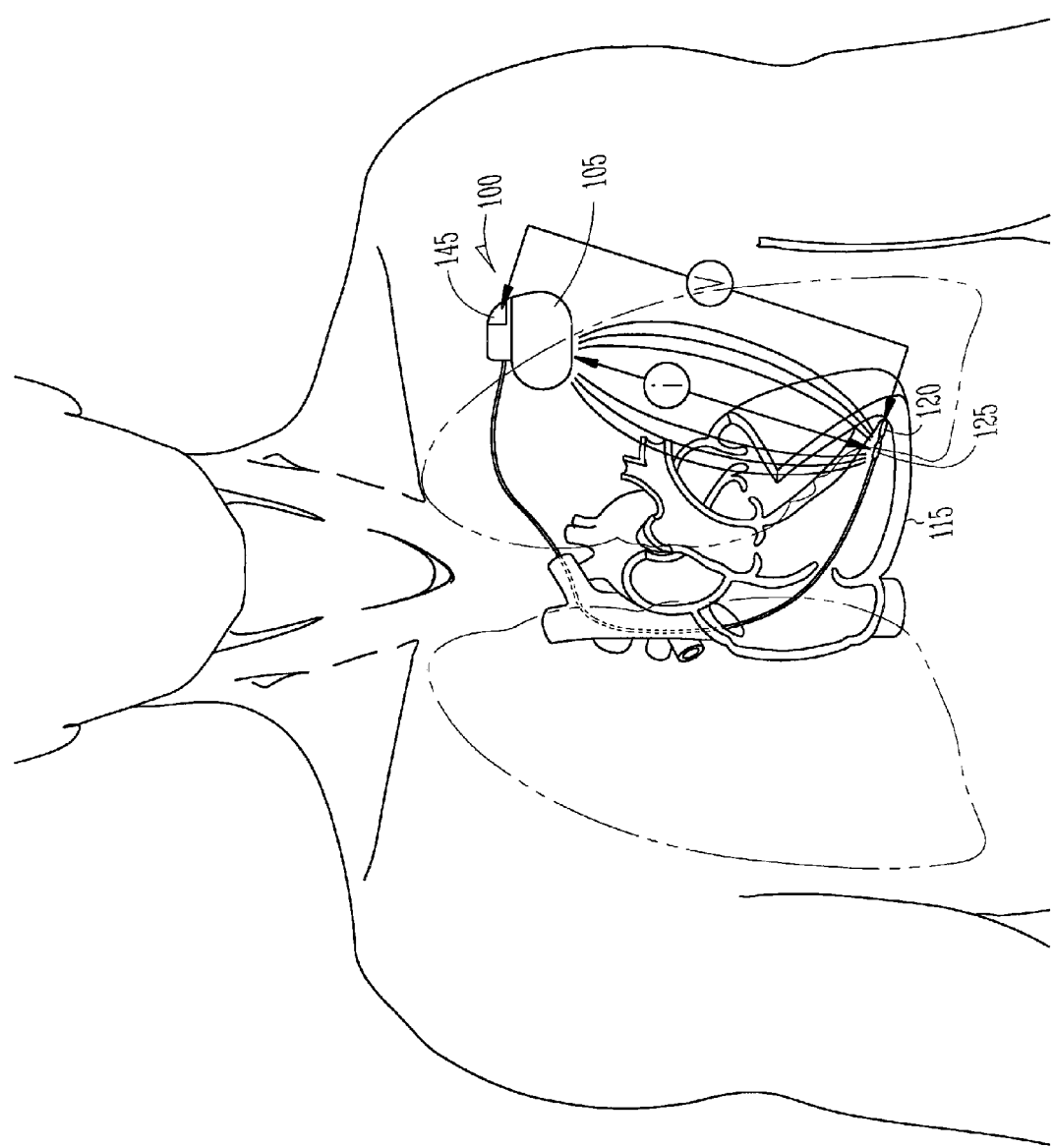
FIG. 2 illustrates an embodiment of the system implanted in a thorax region.

FIG. 2 illustrates the system 100 implanted in the thorax region of a patient. It can be seen from the positioning of pulse generator 105 and lead electrodes 120 and 125 that the system 100 measures the impedance across a substantial portion of the patient's thorax. In one embodiment of the system 100, a time index is stored along with the impedance value obtained. The time index and impedance value are then used to derive a lung tidal volume. As discussed in the Hartley patent, lung tidal volume is obtained by taking the difference between the maximum and minimum impedance values stored for the patient's previous breath. A larger tidal volume value indicates a deeper breath for the patient than a smaller tidal volume value. In another embodiment, respiratory rate is derived from the impedance signal. One method to obtain respiratory rate would be to determine the time interval between maximum impedance values over a period of time and convert the data to breaths per minute. Based on information from the lung tidal volume and respiratory rate, controller 165 adjusts the rate of the delivery of therapy to the heart 115. A further embodiment of the system 100 is a combination of cardiac rhythm management and treatment for sleep apnea. In this embodiment, the system 100 determines if the respiratory activity falls below a predetermined level. If the respiratory activity falls below the predetermined level, the system provides therapy to treat the sleep apnea such as diaphragmatic pacing. An apparatus for diaphragmatic pacing to treat sleep apnea is described in Scheiner et al., U.S. Pat. No. 6,415,183 "A METHOD AND APPARATUS FOR DIAPHRAGMATIC PACING," assigned to the assignee of the present application and which is incorporated herein by reference.

Figure 3:
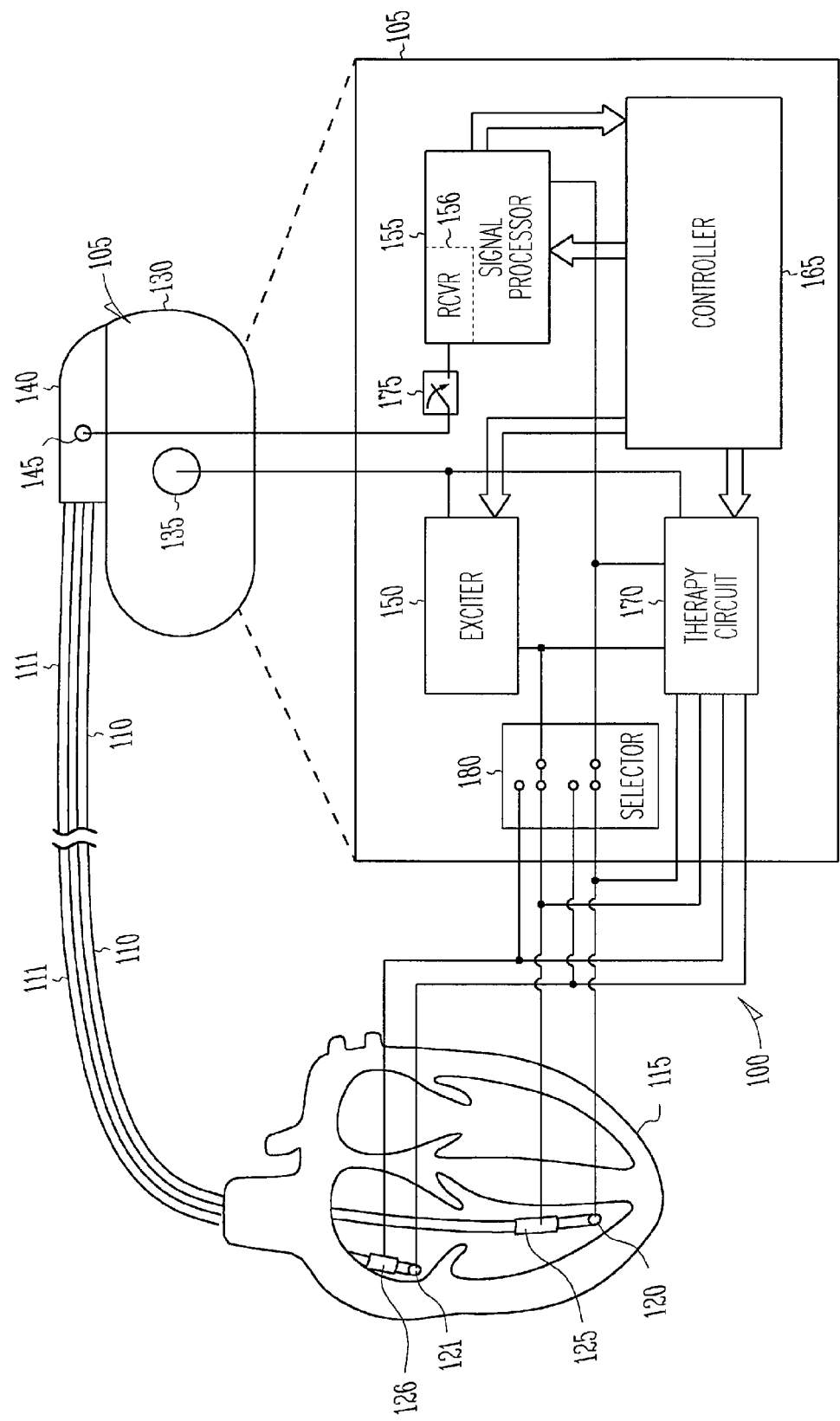
FIG. 3 shows a block diagram of a multi-lead embodiment of the system.

FIG. 3 shows an embodiment of the system 100 that uses multiple endocardial leads 100, 111. Leads 110, 111 are multi-conductor leads and include tip electrodes 120, 121 coupled to a first conductor and ring electrodes 125, 126 coupled to a second lead conductor within their respective lead. In the embodiment shown, lead 110 is implanted in the right ventricle of a heart 115 and lead 111 is implanted in the right atrium of the heart. If lead 111 is used to measure the impedance, the impedance sampling may begin, for example, at a fiducial marker indicating the onset of the P-wave rather than the QRS complex or the peak of an R-wave.

This embodiment of the system 100 further shows a pulse generator 105 that includes selector 180. Selector 180 is able to change the electrode combination providing the stimulus from a combination including ring electrode 125 to a combination including ring electrode 126. Selector 180 also changes the electrode combination measuring the stimulus response from a combination including tip electrode 120 to a combination including tip electrode 121. This ability to change the electrode combination is useful if, for example, measuring the sensed response using tip electrode 120 proves to be difficult due to signal noise, and use of another combination of electrodes provides a better measurement. It should be noted that other embodiments of the system 100 deliver the current stimulus or measure the response between any other suitable combinations of electrodes.

Figure 4:
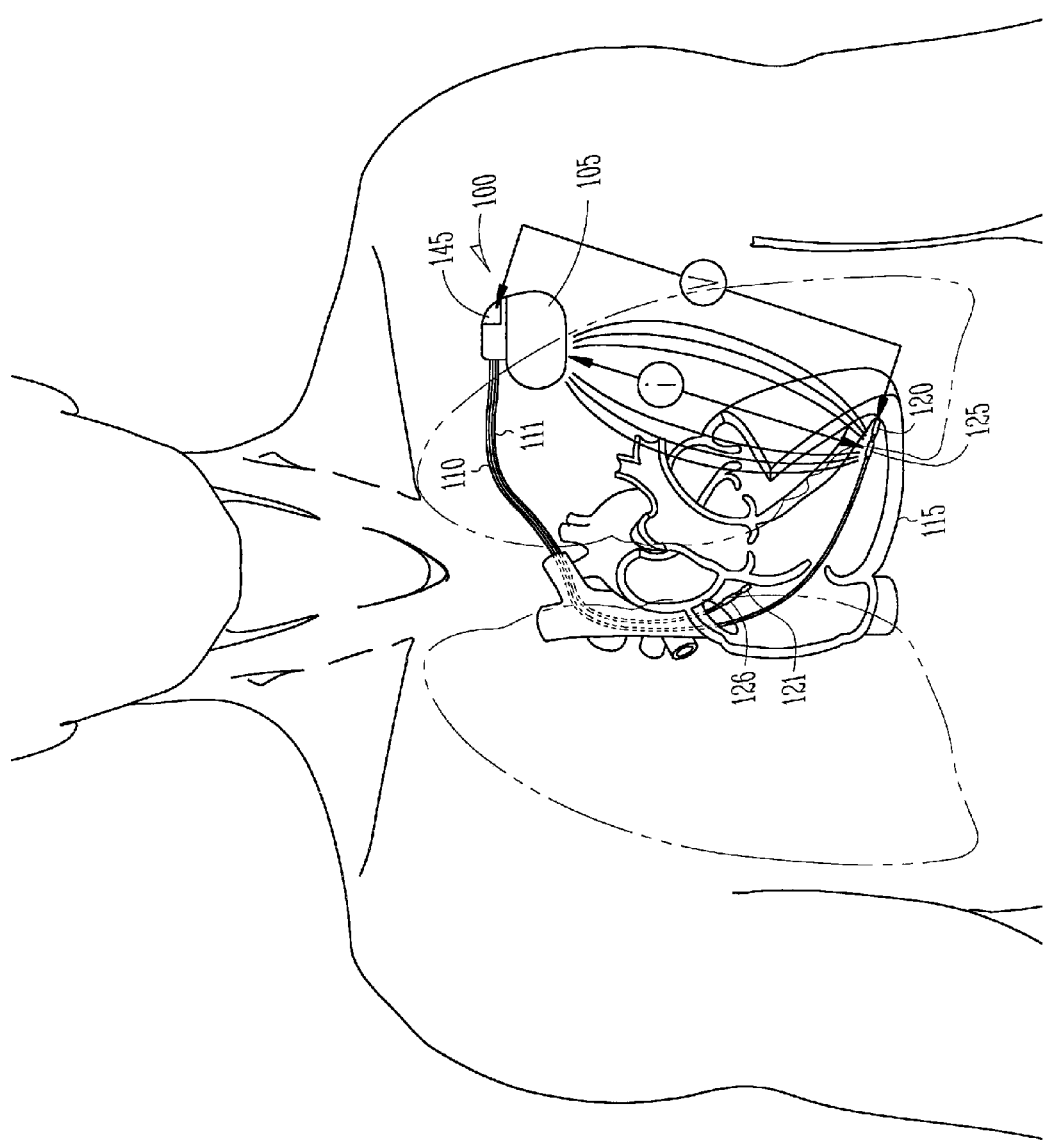
FIG. 4 illustrates a multi-lead embodiment of the system implanted in a thorax region.

FIG. 4 illustrates a multiple lead embodiment of the system 100 implanted in the thorax region of a patient. It can be seen from the positioning of pulse generator 105 and lead electrodes 120, 121 and 125, 126 that the system 100 measures the impedance across a substantial portion of the patient's thorax. It can also be seen that selecting different combinations of electrodes will result in an impedance measurement taken across different vectors of the thorax. For example, using tip and ring electrodes 121, 126 and header and can electrodes 145, 135 will measure impedance across a vector originating from the atrium, while using tip and ring electrodes 120, 125 and can electrodes 145, 135 will measure impedance across a vector originating from the ventricle. Thus, it is beneficial for the system 100 to have flexibility in its measurement configuration to take full advantage of its positioning.

Figure 5:
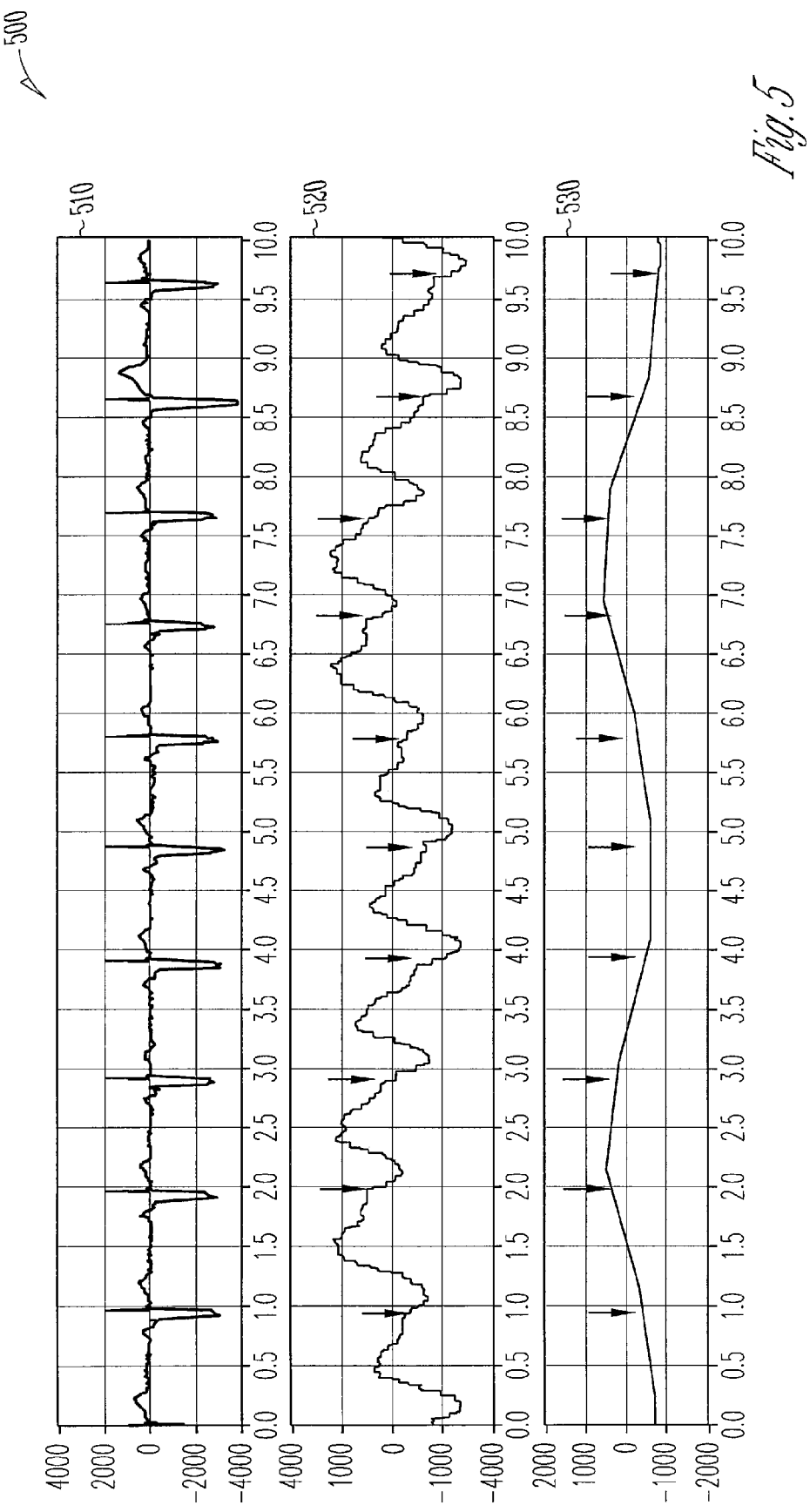
FIG. 5 is a representation of a transthoracic impedance signal sampled in a predetermined time relationship to a fiducial marker.

FIG. 5 is a graphical illustration 500 of sampling the transthoracic impedance synchronously to fiducial markers that indicate R-wave peaks. QRS complexes from heart activity are shown in graph 510. In graph 520, a transthoracic impedance signal obtained by sampling every 50 milliseconds is shown. The variation of the impedance signal with cardiac stroke volume can be seen. It can also be seen that the higher frequency stroke volume component is superimposed onto a lower frequency respiratory component. The downwardly pointing arrows shown in graph 520 correspond to the occurrence of R-waves in graph 510. Graph 530 shows the impedance signal obtained when the impedance is sampled synchronously to the R-waves. Graph 530 shows that the lower frequency respiratory signal is extracted from the higher frequency stroke volume component.

Figure 6:
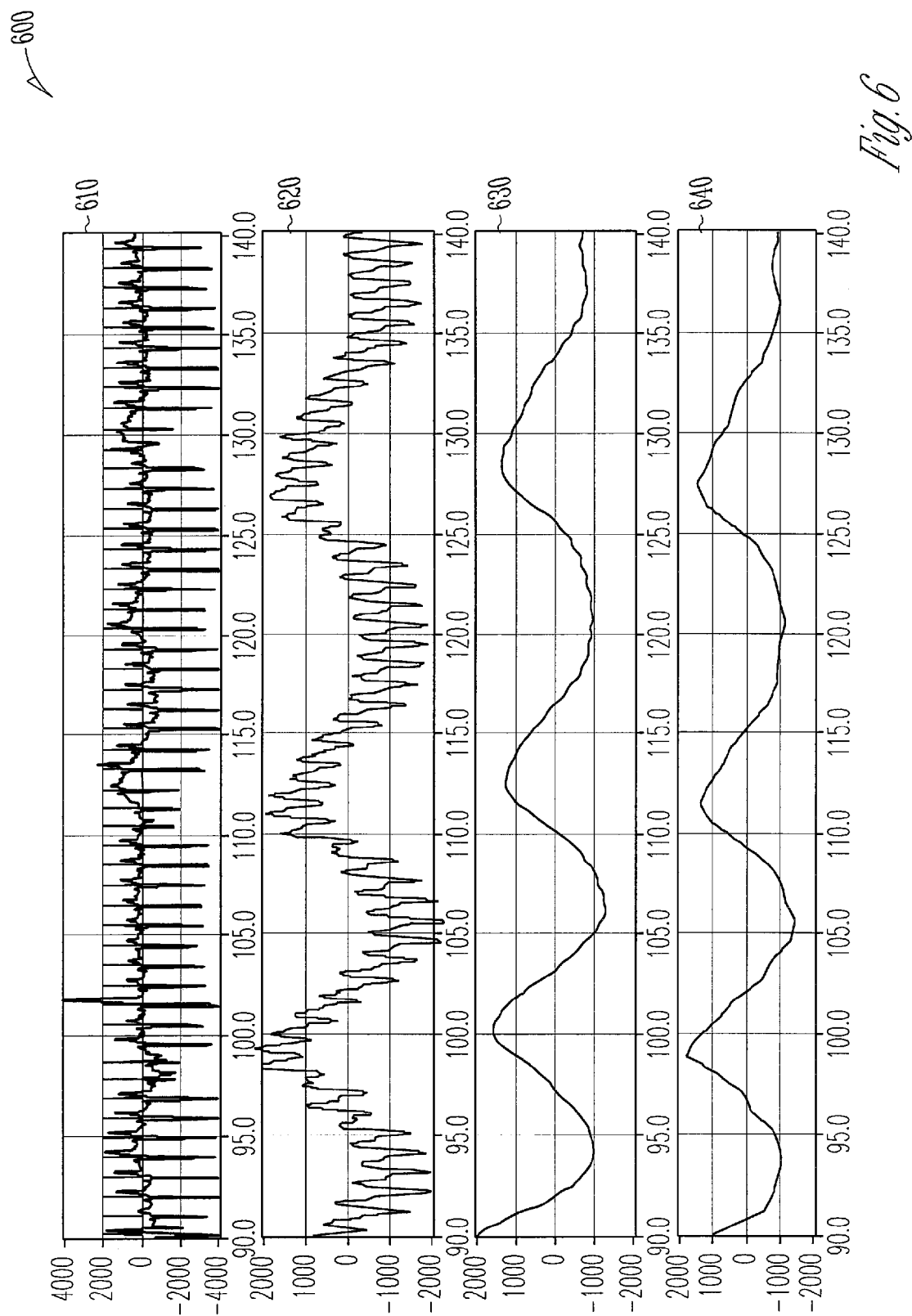
FIG. 6 is an illustration of a filtered transthoracic impedance signal compared to an R-wave synchronized sampled impedance signal during deep and slow breathing.

FIG. 6 is a graphical illustration 600 of sampling the transthoracic impedance during deep and slow breathing. Graph 610 shows the R-waves from heart activity. Graph 620 shows the transthoracic impedance signal obtained by sampling at a frequency high enough to obtain both the stroke volume and the respiratory component. Graph 630 shows the respiratory component obtained through sampling and filtering with a $4^{th}$-order Elliptic Low Pass Filter with the filter pole at 0.2 Hertz(Hz). In implantable devices, such filters are generally implemented with active circuits. While these circuits can be designed to operate at low power, even low power circuits have an appreciable effect on battery life when the implanted period is on the order of five years. Graph 640 shows the respiratory component obtained with R-wave synchronous sampling. Graphs 630 and 640 show that similar results are obtained concerning phase, amplitude and frequency using the low pass filtering method and the R-wave sampling method. Thus, similar results for impedance measurements at slow and deep breathing can be attained while conserving the power required by an active low pass filtering circuit.

Figure 7:
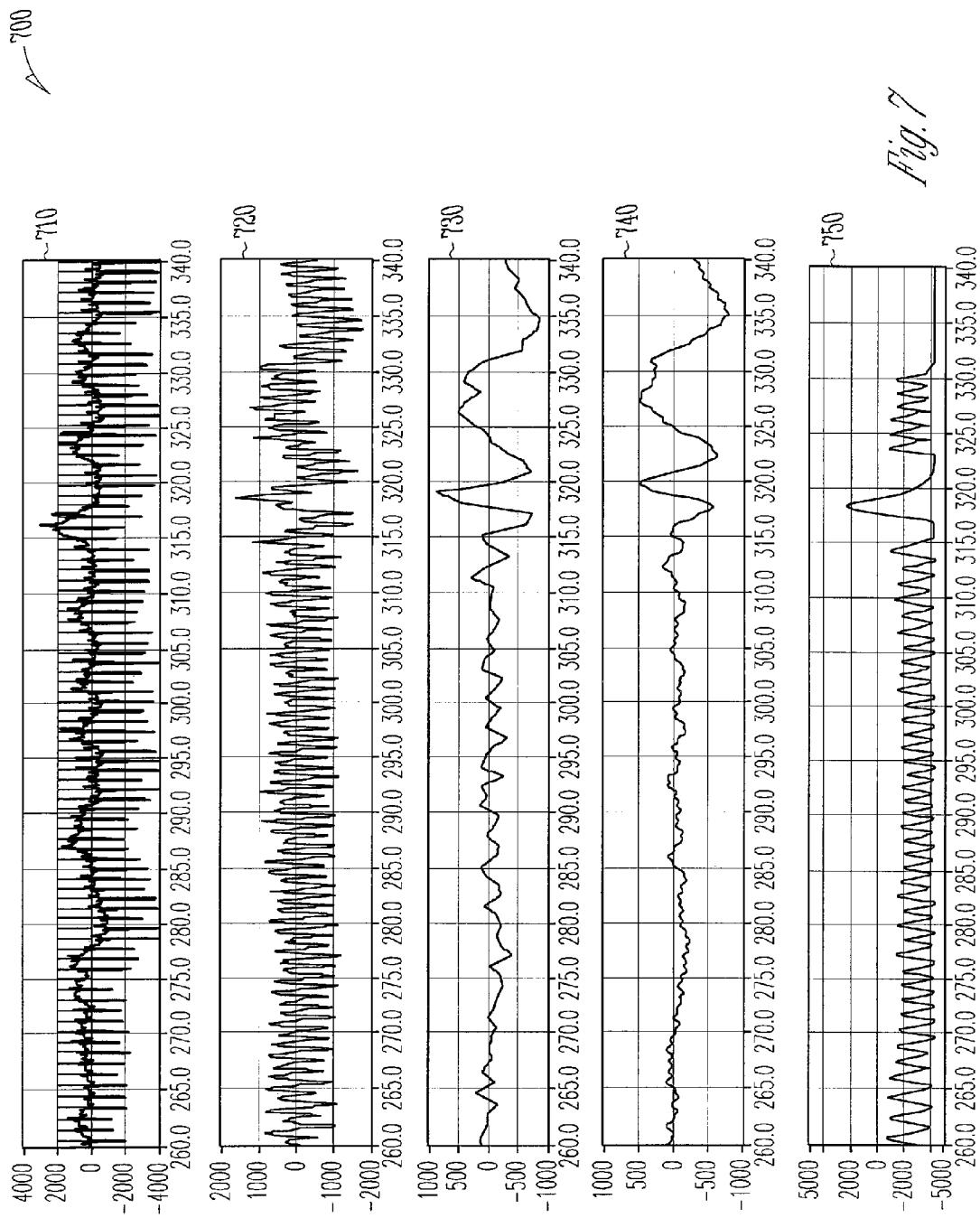
FIG. 7 is an illustration of a filtered transthoracic impedance signal compared to an R-wave synchronized sampled impedance signal during fast and shallow breathing.

FIG. 7 is a graphical illustration 700 of sampling the transthoracic impedance during fast and shallow breathing. Graph 710 shows the R-waves of heart activity. Graph 720 shows the transthoracic impedance signal obtained by sampling at a frequency high enough to obtain both the stroke volume and the respiratory component. Graph 730 shows the respiratory component obtained with R-wave synchronous sampling. Graph 740 shows the respiratory component obtained from the high frequency sampling filtering with a $4^{th}$-order Elliptic Low Pass Filter with the filter pole at 0.2 Hertz (Hz). Graph 750 shows the actual measured air volume passing through the lungs of the patient. A comparison of graphs 740 and 750 shows that in attempting to capture the transthoracic impedance during fast and shallow breathing, a 0.2 Hz pole can mask some of the impedance information as the frequency of the respiratory activity approaches the frequency of the stroke volume. Graph 730 shows that R-wave synchronous sampling has some advantage in reproducing amplitude information. This is because the sampling increases with the heart rate of the patient. Thus, somewhat improved results for impedance measurements at fast and shallow breathing can be attained while conserving the power required by an active low pass filtering circuit.

Figure 8:
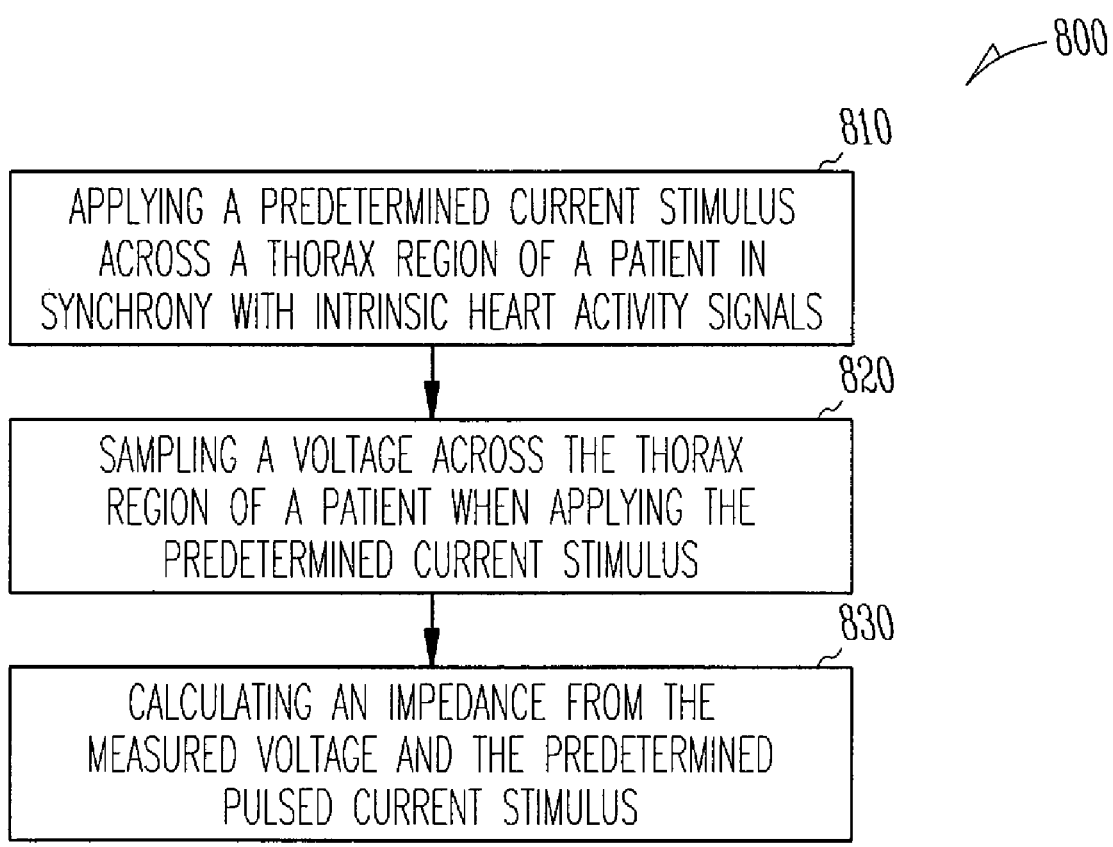
FIG. 8 is a flow chart illustrating a method of measuring transthoracic impedance.

FIG. 8 is a flow chart illustrating a method 800 of measuring transthoracic impedance. At 810, a predetermined pulsed current stimulus is applied across a thorax region of a patient in synchrony with intrinsic heart activity signals. At 820, a voltage across the thorax region is sampled when applying the predetermined pulsed current stimulus. At 830, impedance is calculated from the measured voltage and the predetermined pulsed current stimulus.

Figure 9:
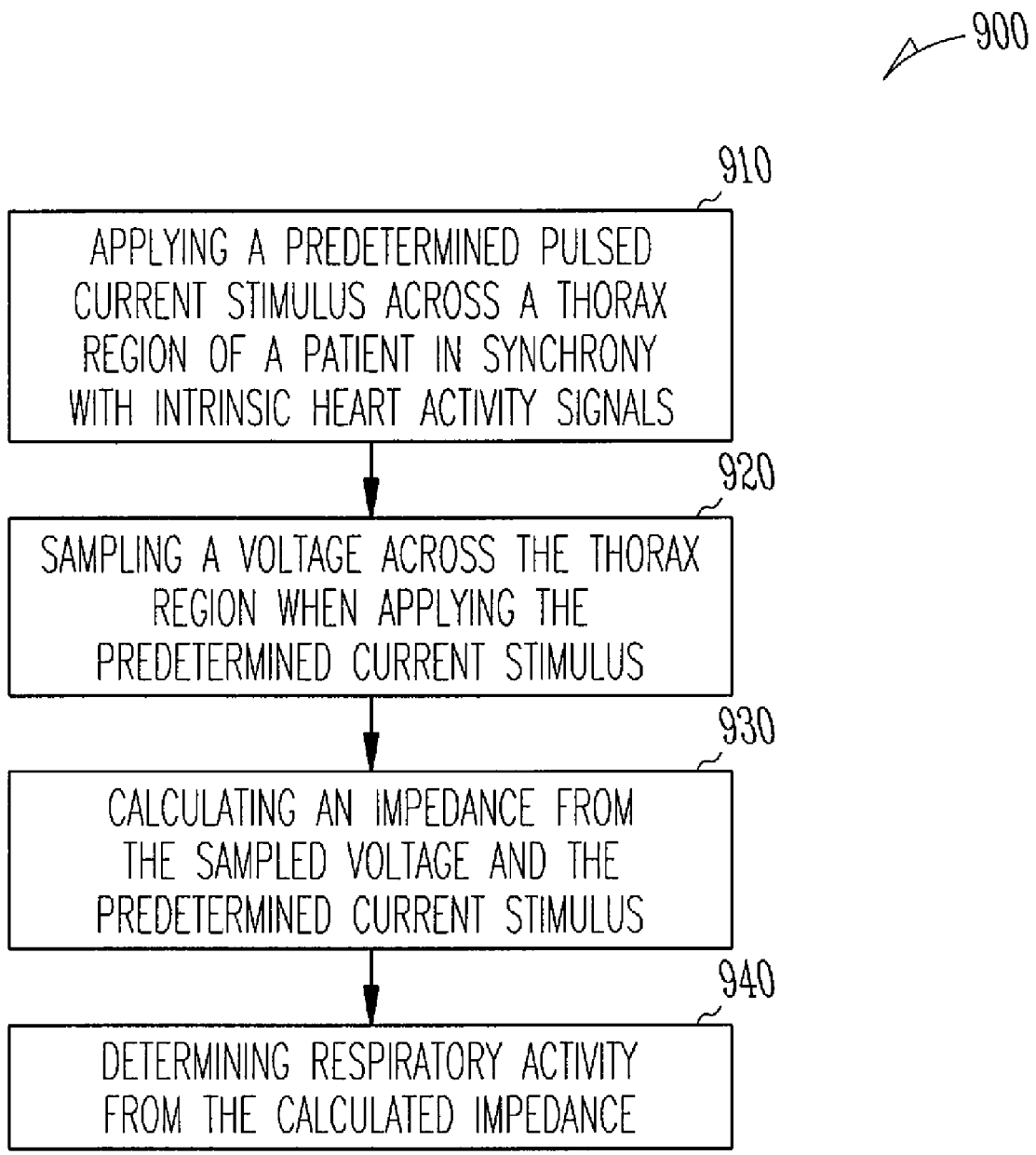
FIG. 9 is a flow chart illustrating a method of monitoring lung ventilation.

FIG. 9 is a flow chart illustrating a method of monitoring lung ventilation. At 910, a predetermined pulsed current stimulus is applied across a thorax region of a patient in synchrony with intrinsic heart activity signals. At 920, a voltage across the thorax region is sampled when applying the predetermined current stimulus. At 930, impedance is calculated from the sampled voltage and the predetermined current stimulus. At 940, respiratory activity is determined from the calculated impedance.

Although specific examples have been illustrated and described herein, it will be appreciated by those of ordinary skill in the art that any arrangement calculated to achieve the same purpose could be substituted for the specific example shown. This application is intended to cover any adaptations or variations of the present invention. Therefore, it is intended that this invention be limited only by the claims and the equivalents shown.

What is claimed is:

1. A cardiac rhythm management device, comprising:
   a sensor for obtaining a signal indicative of an action of a heart;
   an impedance measurement circuit adapted to measure transthoracic impedance;
   means for processing the signal indicative of the action of the heart to sample the transthoracic impedance at sampling intervals commenced by fiducial markers in the signal indicative of the action of the heart, the sampling of the impedance signal removing the component of a stroke volume of the heart from the signal and thereby providing ventilation information; and
   a therapy circuit for generating and delivering cardiac rhythm management therapy to a patient.

2. The device of claim 1, wherein the fiducial marker is an onset of a P-wave.

3. The device of claim 1, wherein the fiducial marker is an onset of a QRS complex.

4. The device of claim 1, wherein the fiducial marker is an R-wave peak.

5. The device of claim 1, wherein the fiducial marker is a T-wave peak.

6. The device of claim 1, wherein the ventilation information is a signal indicative of respiratory activity.

7. The device of claim 1, wherein the device adjusts a rate of delivering cardiac rhythm management therapy based on ventilation information provided by the sampled impedance signal.

8. The device of claim 1, wherein the sampled values of the impedance signal are combined to reconstruct an impedance signal that removes the stroke volume component and represents respiratory activity.

9. A cardiac rhythm management system comprising:
   at least one endocardial lead adapted to be coupled to a plurality of locations in a thorax of a patient, wherein the at least one endocardial lead includes at least one electrode; and
   a cardiac rhythm management device coupled to the at least one endocardial lead, wherein the cardiac rhythm management device includes:
      an exciter adapted to deliver a pulsed current stimulus to an endocardial lead;
      a signal processor programmed to detect fiducial markers in a signal indicative of the action of the heart, and wherein the signal processor also includes a receiver adapted to obtain transthoracic impedance information responsive to the pulsed current stimulus;
      a sampling element coupled to the receiver and adapted to cause the receiver to obtain transthoracic impedance in response to an occurrence of a fiducial marker; and
      a housing for the cardiac rhythm management device, an outer surface of the housing further comprising a housing electrode, wherein the housing electrode is coupled to the exciter.

10. The system of claim 9, wherein the cardiac rhythm management device further includes:
    a therapy circuit, coupled to the at least one endocardial lead, wherein the lead is adapted to be coupled to a heart of a patient for delivering cardiac rhythm management therapy thereto; and
    a controller, coupled to the therapy circuit for adjusting a rate of delivery of the cardiac rhythm management therapy based on the sampled transthoracic impedance.

11. The system of claim 9, wherein the signal processor further includes a memory, and wherein the signal processor measures a time interval from a past occurrence of a fiducial marker to a present occurrence of the fiducial marker and stores a value in the memory representative of the measured impedance in association with the measured time interval.

12. The system of claim 11, wherein the value representative of the measured impedance in association with the measured time interval is included in an estimation of lung tidal volume.

13. The system of claim 11, wherein the value representative of the measured impedance in association with the measured time interval is included in a determination a respiratory rate.

14. The system of claim 9, wherein the system further includes a header, coupled to the housing for receiving the at least one endocardial lead, and carrying a header electrode, wherein the header electrode is coupled to the sampling element.

15. The system of claim 14, wherein the exciter applies the pulsed current stimulus from a first endocardial lead electrode across the thorax region of the patient to the housing electrode, and a second endocardial lead electrode and the header electrode are in communication with the receiver for obtaining transthoracic impedance information responsive to the pulsed current stimulus across the thorax region of the patient.

16. The system of claim 15, wherein the pulsed current stimulus is applied as a vector directed from a lead electrode adaptable to be placed in a patient's atrium to the housing of the cardiac rhythm management device.

17. The system of claim 15, wherein the pulsed current stimulus is applied as a vector directed from a lead electrode adaptable to be placed in a patient's atrium to the header of the cardiac rhythm management device.

18. The system of claim 15, wherein the pulsed current stimulus is applied as a vector directed from a lead electrode adaptable to be placed in a patient's ventricle to the housing of the cardiac rhythm management device.

19. The system of claim 15, wherein the pulsed current stimulus is applied as a vector directed from a lead electrode adaptable to be placed in a patient's ventricle to the header of the cardiac rhythm management device.

20. The system of claim 9, wherein the cardiac rhythm management device further includes a selector, wherein the selector is operable to couple the exciter and signal processor to a selected lead, wherein the exciter is coupled to an electrode of one endocardial lead and the signal processor is coupled to a different electrode, and wherein selecting a different lead causes the exciter to apply the pulsed current stimulus as a different vector in the thorax.

21. A method of measuring transthoracic impedance, the method comprising:
    detecting fiducial markers in a signal indicative of an action of a heart;
    applying a predetermined pulsed current stimulus across a thorax region of a patient in a predetermined time relationship to an occurrence of a fiducial marker;
    sampling a voltage across the thorax region while applying the predetermined pulsed current stimulus, such that a component of the voltage from a stroke volume of the heart is substantially constant; and
    calculating an impedance from the sampled voltage and the current stimulus.

22. The method of claim 21, wherein the fiducial marker is an onset of a P-wave.

23. The method of claim 21, wherein the fiducial marker is an onset of a QRS complex.

24. The method of claim 21, wherein the fiducial marker is an R-wave peak.

25. The method of claim 21, wherein the fiducial marker is a T-wave peak.

26. The method of claim 21, wherein the method further includes:
    storing data representations of the impedance;
    measuring a time interval from a first occurrence of a fiducial marker to a second occurrence of the fiducial marker; and
    storing the time interval in association with the data representations of the impedance.

27. The method of claim 26, wherein the method further includes estimating a lung tidal volume from the stored impedance values and the stored time intervals.

28. The method of claim 21, wherein the applying the predetermined pulsed current stimulus across a thorax region of a patient includes placing stimulus-applying electrodes at locations selected to define a vector across the thorax region.

29. The method of claim 21, wherein the applying the predetermined pulsed current stimulus includes applying the current stimulus from a first electrode across the thorax region to a second electrode, and wherein the sampling a voltage includes measuring a voltage between a third electrode and a fourth electrode positioned on both sides of the thorax region.

30. The method of claim 21, further including changing a therapy delivered in a system for treating cardiac arrhythmia based on the calculated impedance.

31. The method of claim 30, wherein the changing a therapy delivered includes adjusting the minimum pacing rate.

32. A cardiac rhythm management system comprising:
a plurality of endocardial leads adapted to be coupled to a plurality of locations in a thorax of a patient, wherein each of the plurality of endocardial leads includes at least one stimulus-applying electrode; and
a cardiac rhythm management device coupled to the plurality of endocardial leads, wherein the cardiac rhythm management device includes:
a housing for the cardiac rhythm management device, an outer surface of the housing further comprising a further electrode;
an exciter, coupled to the electrodes and adapted to deliver a pulsed current stimulus from the endocardial lead electrodes to the housing electrode;
a signal processor in communication with the electrodes and programmed to detect fiducial markers in a signal indicative of an action of a heart, and wherein the signal processor also includes a receiver adapted to obtain transthoracic impedance information responsive to the current stimulus; and
means for sampling the transthoracic impedance in response to the occurrence of a fiducial marker in the signal indicative of the action of the heart.

33. The system of claim 32, wherein the endocardial leads further include a first electrode and a second electrode and the cardiac rhythm management device further includes a selector coupled to the exciter and signal processor, wherein the selector is operable to couple the exciter and signal processor to a selected lead, wherein the exciter is coupled to the first electrode of the selected lead and the sampling means is coupled to the second electrode of the selected lead, and wherein selecting a different lead causes the exciter to apply the pulsed current stimulus as a different vector across the thorax to the housing electrode.

34. The system of claim 32, wherein the receiver measures voltage in response to the pulsed current stimulus.

35. A method of treating lung ventilation disorders, the method comprising:
detecting fiducial markers in a signal indicative of an action of a heart;
applying a predetermined pulsed current stimulus across a thorax region of a patient in a predetermined time relationship to the fiducial markers;
sampling a voltage across the thorax region while applying the predetermined current stimulus;
calculating impedance from the sampled voltage and the current stimulus;
determining respiratory activity from the calculated impedance;
determining if the respiratory activity falls below a predetermined level; and
providing a therapy for stimulating breathing activity if the respiratory activity falls below the predetermined level.

36. The method of claim 35, wherein the determining respiratory activity includes calculating a respiratory rate.

37. The method of claim 35, wherein the determining respiratory activity includes calculating respiratory rate and tidal volume.

38. The method of claim 35, wherein the providing a therapy delivered for treating sleep apnea includes providing diaphragmatic pacing.

39. The method of claim 35, wherein the calculating impedance from the measured voltage and the predetermined current stimulus further includes:
storing data representations of impedance;
measuring a time interval from a first occurrence of a fiducial marker to a second occurrence of the fiducial marker; and
storing the time interval in association with the data representations of impedance.

40. The method of claim 39, wherein the determining respiratory activity from the calculated impedance includes estimating a lung tidal volume from the data representations of impedance and the stored time intervals.

41. A method of measuring a transthoracic impedance, the method comprising:
detecting fiducial markers in a signal indicative of the action of the heart;
a step of applying a predetermined pulsed current stimulus across a thorax region of a patient in a fixed relationship to the occurrence of a fiducial marker;
sampling a voltage across the thorax region when applying the predetermined pulsed current stimulus, such that a component of the voltage from a stroke volume of the heart is substantially constant; and
calculating an impedance from the measured voltage and the predetermined pulsed current stimulus.

42. The method of claim 41, wherein the step of applying a current stimulus is initiated in a fixed relationship to the occurrence of an onset of a P-wave.

43. The method of claim 41, wherein the step of applying a current stimulus is initiated in a fixed relationship to the occurrence of an onset of a QRS complex.

44. The method of claim 41, wherein the step of applying a current stimulus is initiated in a fixed relationship to the occurrence of an R-wave peak.

45. The method of claim 41, wherein the step of applying a current stimulus is initiated in a fixed relationship to the occurrence of a T-wave peak.

* * * * *